US012706201B2

(12) United States Patent
Yin

(10) Patent No.: US 12,706,201 B2
(45) Date of Patent: Aug. 11, 2026

(54) FINGER MOTION EXERCISE ASSISTING APPARATUS AND FINGER MOTION EXERCISE ASSISTING METHOD

(71) Applicant: MAXELL, LTD., Kyoto (JP)

(72) Inventor: Ying Yin, Beijing (CN)

(73) Assignee: MAXELL, LTD., Kyoto (JP)

( * ) Notice: Subject to any disclaimer, the term of this patent is extended or adjusted under 35 U.S.C. 154(b) by 116 days.

(21) Appl. No.: 17/619,764

(22) PCT Filed: Jun. 15, 2020

(86) PCT No.: PCT/CN2020/096087
§ 371 (c)(1),
(2) Date: Dec. 16, 2021

(87) PCT Pub. No.: WO2020/253645
PCT Pub. Date: Dec. 24, 2020

(65) Prior Publication Data

US 2022/0359055 A1 Nov. 10, 2022

(30) Foreign Application Priority Data

Jun. 17, 2019 (CN) ........................ 201910520894.X

(51) Int. Cl.
*G16H 20/30* (2018.01)

(52) U.S. Cl.
CPC .................................. *G16H 20/30* (2018.01)

(58) Field of Classification Search
None
See application file for complete search history.

(56) References Cited

U.S. PATENT DOCUMENTS

2009/0192021 A1* 7/2009 Wu .................... A63B 24/0062 482/4
2011/0054361 A1* 3/2011 Sakoda ................ A61B 5/4082 600/595

(Continued)

FOREIGN PATENT DOCUMENTS

CN 105832343 A 8/2016
CN 107491648 A 12/2017

(Continued)

OTHER PUBLICATIONS

R. Colombo et al., "The SonicHand Protocol for Rehabilitation of Hand Motor Function: A Validation and Feasibility Study," IEEE Transactions on Neural Systems and Rehabilitation Engineering, Apr. 2019, vol. 27, No. 4, pp. 664-672, , doi: 10.1109/TNSRE.2019.2905076 (Year: 2019).*

(Continued)

*Primary Examiner* — Rachel L. Porter
(74) *Attorney, Agent, or Firm* — MATTINGLY & MALUR, PC

(57) ABSTRACT

A finger motion exercise assisting apparatus and related method receive input information from an external device. A prompter prompts a test subject with a prompt instruction to perform a finger motion exercise; and a finger motion catcher is used to catch finger motion data of the test subject. A finger motion analyzer includes an exercise item generator, a motion parameter calculator, and a finger function evaluator. On the basis of the input information, one or more exercise items are generated and an arranging order for the exercise items is determined. Each exercise item includes one or more prompt instructions. On the basis of the finger motion data, the motion parameter calculator calculates motion parameters characterizing a finger motion for each exercise item. Further, on the basis of the input information, (Continued)

the finger function evaluator compares the motion parameters with a motion parameter database, and outputs a comparison result.

8 Claims, 7 Drawing Sheets

(56) References Cited

U.S. PATENT DOCUMENTS

2013/0060166 A1 3/2013 Friedman et al.
2013/0143718 A1 * 6/2013 Pani .................. A63B 21/4035 482/8
2020/0222756 A1 * 7/2020 Sano .................... A61B 5/4088

FOREIGN PATENT DOCUMENTS

CN 108634957 A 10/2018
CN 109152556 A 1/2019
JP 2017217244 A 12/2017
WO WO 9000879 A1 * 2/1990
WO WO-2017212719 A1 * 12/2017 ............... A61B 5/11

OTHER PUBLICATIONS

Akihiko Kandori, Masaru Yokoe, Saburo Sakoda, Kazuo Abe, Tsuyoshi Miyashita, Hiroshi Oe, Hiroaki Naritomi, Kuniomi Ogata, Keiji Tsukada; "Quantitative magnetic detection of finger movements in patients with Parkinson's Disease;" Neuroscience Research, vol. 49, Issue 2, Jun. 2004, pp. 253-260 (Year: 2004).*
International Search Report of PCT/CN2020/096087 dated Sep. 18, 2020.
Chinese Office Action received in corresponding Chinese Application No. 201910520894.X dated May 30, 2025.
Na Shuxun et al., "Modern University Sports Theory and Practice", 2010, Guangdong Higher Education Press, Guangzhou.

* cited by examiner

Fig.4

| finger numbers | |
|---|---|
| left thumb | 1 |
| left index finger | 2 |
| left middle finger | 3 |
| left ring finger | 4 |
| left pinky | 5 |
| right thumb | 6 |
| right index finger | 7 |
| right middle finger | 8 |
| right ring finger | 9 |
| right pinky | 10 |

FINGER MOTION EXERCISE ASSISTING APPARATUS AND FINGER MOTION EXERCISE ASSISTING METHOD

TECHNICAL FIELD

This invention relates to a finger motion exercise assisting apparatus and a finger motion exercise assisting method.

BACKGROUND ART

The sequelae of some diseases and trauma can cause paralysis of the hands and feet of patients. It is necessary to evaluate the motion function of the patients' fingers when investigating the rehabilitation of the disease. On the other hand, some diseases are also accompanied by intellectual impairment and/or mental behavior impairment. Therefore, in evaluating the motion function of the patient's fingers, it is also necessary to consider the patient's response to instructions.

Therefore, a system is being developed for easily evaluating a person's cognitive function and motion function by measuring and analyzing the motion of a human finger. For example, Patent Document 1 discloses a technique for generating and prompting an appropriate exercise menu for maintaining or improving a person's cognitive function and motion function, thereby assisting the person's exercise. In this technology, if a test subject's finger is wearing a sensor, it is required to let the person to perform a finger tapping motion, or use a touchpad terminal to measure and evaluate the person's finger motion.

CITATION LIST

Patent Document

Patent Document 1: Japanese Patent Application Publication No. JP2017-217244

SUMMARY OF THE INVENTION

Technical Problems

In the technique of Patent Document 1, if a test subject's thumb is injured or missing, it is difficult for the person to perform a finger motion exercise, and a linkage between the fingers is insufficient. On the other hand, regarding an older test subject, it is difficult to smoothly collect data because he or she is unfamiliar with the use of touchpad terminals.

Solutions to Problems

In view of the above-discussed problems, the present invention relates to a finger motion exercise assisting apparatus, which is used to assists a test subject in finger motion exercise, said apparatus comprising:

an operation input receiver, which receives input information of an operator from outside, said input information including an exercise purpose;

a prompter, which indicates a test subject a prompt instruction for performing a finger motion exercise;

a finger motion catcher, which is used to catch finger motion data of the test subject's finger motion performed according to the prompt instruction; and a finger motion analyzer, which includes a data processor and a storage, said data processor including an exercise item generator, a motion parameter calculator, and a finger function evaluator, wherein:

the exercise item generator, in accordance with the input information, generates one or more exercise items and determines an arranging order for the exercise items, with each exercise item including one or more of the prompt instructions, the motion parameter calculator, in accordance with the finger motion data and with respect to each exercise item generated by the exercise item generator, calculates a motion parameter characterizing a finger motion, the finger function evaluator, in accordance with the input information, compares the motion parameter with the motion parameter database stored in the storage, and outputs a comparison result.

According to this aspect of the present invention, it is possible to provide a finger motion exercise assisting apparatus that does not impose a large burden on a test subject.

The finger motion exercise assisting apparatus may be configured such that:

the exercise purpose is rehabilitation training or flexibility evaluation, when the exercise purpose is rehabilitation training, the finger function evaluator uses the test subject's historical motion parameter database in the motion parameter database to perform the comparison, when the exercise purpose is flexibility evaluation, the finger function evaluator uses a standard motion parameter database in the motion parameter database to perform the comparison.

According to this aspect of the present invention, it is possible to provide different exercise items according to different exercise purposes, and to process data in a targeted manner, so that it is possible to more accurately respond to actual needs of an operator, thus evaluating the test subject's fingers motion function.

The finger motion exercise assisting apparatus may be configured such that:

the exercise item includes at least one of a single-hand exercise and a two-hand exercise, said single-hand exercise including at least one of a single-finger exercise and a multiple-finger exercise.

According to this aspect of the present invention, it is possible to provide an exercise item involving a linkage between a single finger and multiple fingers, thereby making it possible to more comprehensively evaluate a test subject's finger motion function.

The finger motion exercise assisting apparatus may be configured such that:

the prompt instructions include at least one of: one-hand sequence prompt, one-hand random prompt, one-hand number prompt, two-hand synchronism sequence prompt, two-hand sequence prompt, two-hand synchronism random prompt, two-hand complete random prompt, two-hand same number prompt, two-hand different number prompt, and descriptive prompt.

According to this aspect of the present invention, it is possible to provide a variety of prompt instructions including single hand, double hands, single finger, and multiple fingers. Therefore, it is possible to evaluate a test subject's finger motion function in multiple directions and in a more comprehensive manner.

The finger motion exercise assisting apparatus may be configured such that:

the input information also contains test subject's information;

the test subject's information includes at least one of test subject's disease name, age and sex.

According to this aspect of the present invention, it is possible to prepare suitable exercise items for each test subject, and to adopt the most appropriate evaluation standards to perform an evaluation for test subjects in different situations, thereby making it possible to more accurately evaluate a test subject's finger motion function.

In addition, the data processor may also include a finger data calibrator which calibrates the finger motion data of test subject, while the motion parameter calculator calculates the motion parameters based on the calibrated finger motion data.

In this way, it is possible to eliminate data deviations caused by different lengths of the fingers of each test subject, thus making it possible to more accurately evaluate the finger motion function of the test subject.

The finger motion exercise assisting apparatus may be configured such that:

the input information also includes an exercise item generation mode, when the exercise item generation mode is automatic generation, the exercise item generator automatically generates one or more exercise items and determines an arranging order for the exercise items, when the exercise generation mode is manual generation, the exercise item generator generates one or more exercise items and determines an arranging order for the exercise items, in accordance with the operator's selection.

According to this aspect of the present invention, it is possible to flexibly change an exercise item generation mode according to the needs of an operator, thereby avoiding a situation in which the stored exercise items do not meet the expectations of an operator and this makes it impossible to perform finger exercises.

This invention also relates to a finger motion exercise assisting method, which is used to assists a test subject in finger motion exercise, said method comprising:

an input information receiving step for receiving input information, said input information including an exercise purpose;

an exercise item generation step which, in accordance with the input information, generates one or more exercise items and determines an arranging order for the exercise items, with each exercise item including one or more prompt instructions for the test subject to perform finger motion exercise;

an exercise execution step which, in accordance with the exercise items and an arranging order generated in the exercise item generation step, indicates the test subject the prompt instruction, and catches finger motion data of the test subject who performed a finger motion in accordance with the prompt instruction;

a motion parameter calculation step which, in accordance with the finger motion data and with respect to each exercise item generated in the exercise item generation step, calculates a motion parameter characterizing a finger motion; and a finger function evaluation step which, in accordance with the input information, compares the motion parameter with the motion parameter database, and outputs a comparison result.

According to this aspect of the present invention, it is possible to provide a finger motion exercise assisting method that does not impose a large burden on a test subject.

The finger motion exercise assisting method may be configured such that:

the exercise purpose is rehabilitation training or flexibility evaluation, the finger function evaluation step is performed in the following manner:

when the exercise purpose is rehabilitation training, the historical motion parameter database of the test subject in the motion parameter database is used for the comparison, when the exercise purpose is flexibility evaluation, the standard motion parameter database in the motion parameter database is used for the comparison.

According to this aspect of the present invention, it is possible to provide different exercise items according to different exercise purposes, to perform data processing in a targeted manner, thus making it possible to more accurately respond to the actual needs of an operator, so as to properly evaluate finger motion function of a test subject.

The finger motion exercises assisting method may be configured such that:

the exercise item includes at least one of a single-hand exercise and a two-hand exercise, with the single-hand exercise including at least one of a single-finger exercise and a multiple-finger exercise.

According to this aspect of the present invention, it is possible to provide exercise items involving a linkage between a single finger and multiple fingers, thereby making it possible to more comprehensively evaluate a test subject's motion function.

The finger motion exercises assisting method be configured such that:

the prompt instructions include at least one of: one-hand sequence prompt, one-hand random prompt, one-hand number prompt, two-hand synchronism sequence prompt, two-hand sequence prompt, two-hand synchronism random prompt, two-hand complete random prompt, two-hand same number prompt, two-hand different number prompt, and descriptive prompt.

According to this aspect of the present invention, it is possible to provide various prompt instructions involving single-hand, double-hands, single-finger, and multiple fingers, thus making it possible to evaluate a test subject's finger motion function in multiple directions and in a more comprehensive manner.

DESCRIPTION OF DRAWINGS

FIG. 4 is a table that associates fingers with numbers.

DESCRIPTION OF EMBODIMENTS

First Embodiment

The first embodiment of the present invention will be described below with reference to FIGS. 1-7

Figure 1:
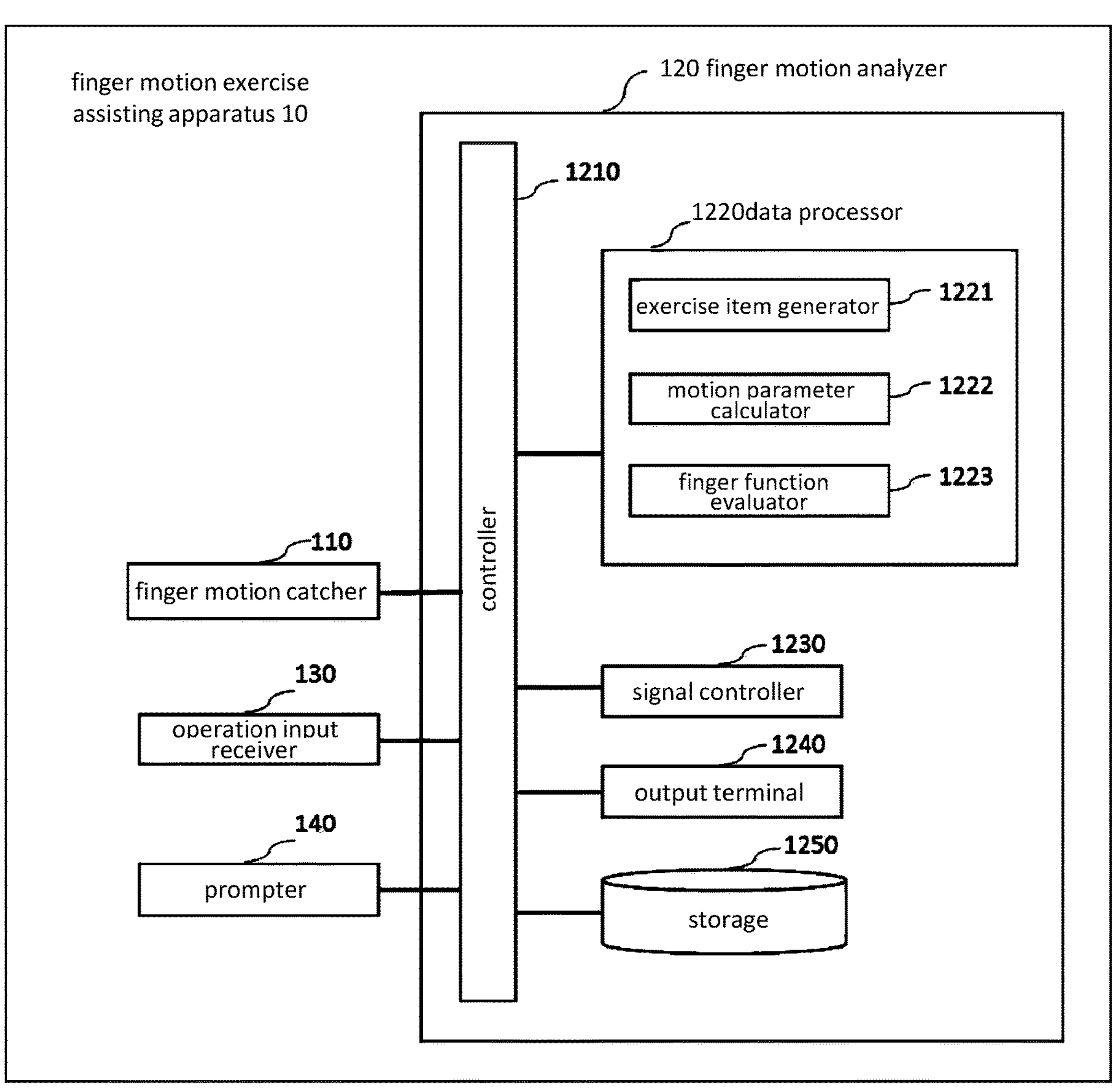
FIG. 1 is an overall configuration diagram of the first embodiment of the present invention.

As shown in FIG. 1, the finger motion exercise assisting apparatus 10 of the present embodiment includes: a finger motion catcher 110 which is used to catch the finger motion data of a test subject; a finger motion analyzer 120; an operation input receiver 130 which receives input information of an operator from the outside; and a prompter 140.

The operation input receiver 130 can be realized by a keyboard, a mouse, a touch screen, or the like. The prompter 140 is used to prompt a test subject to perform the prompted finger motion, and may adopt visual prompts, sound prompts, animation prompts, and waveform prompts. The finger motion catcher 110 catches finger motion data of the test subject's finger motion performed according to the above-mentioned prompt instruction.

In this embodiment, an exercise purpose is taken as the above-mentioned input information, and such an exercise purpose is, for example, a rehabilitation training or a flexibility evaluation. Depending on an exercise purpose selected by an operator, the subsequently generated exercise items, prompt instructions, and evaluation methods to be performed by the finger function evaluator 1223 may also be different.

The finger motion catcher 110 can recognize an open or closed state of a test subject's finger (for example, FIG. 3), using a device such as a magnetic sensor set on the test subject's finger, but the present invention should not be limited as such. In fact, it is also possible to use a device containing a camera and an image analysis module, using an image analysis technique to catch the motion of the test subject's finger. Here, the test subject refers to a test object of the finger motion exercise assisting apparatus 10, which may be an operator or a person different from the operator.

The finger motion analyzer 120 includes a controller 1210, a data processor 1220, a signal controller 1230, an output terminal 1240, and a storage 1250.

The data processor 1220 includes an exercise item generator 1221, a motion parameter calculator 1222, and a finger function evaluator 1223. The controller 1210 is composed of CPU, ROM, RAM and the like, and transmits and controls each signal via the signal controller 1230.

The controller 1210 receives input information from the operation input receiver 130 and sends this information to the exercise item generator 1221. The exercise item generator 1221 generates one or more exercise items and determines an exercise item based on the above input information. An arranging order is stored in the storage 1250. Here, each exercise item includes one or more prompt instructions, and the prompt instructions are used to prompt the test subject to perform finger motion. The prompt instruction is then indicated to the test subject by the prompter 140.

In the present embodiment, it is required to provide an exercise item involving a linkage between a single finger and multiple fingers. Each exercise item includes at least one of the following Case 1-Case 4.

Case 1: Brief evaluation of finger ability.

Case 2: It is required to perform a quick finger opening/closing motion. Namely, it is necessary to let a designated finger to repeat an opening/closing action (shown in FIG. 3) as quickly as possible. The designated finger can be one finger or multiple fingers. The opening/closing motion can be one-hand, simultaneous two-hands or interactive two-hands.

Case 3: It is required to perform a finger opening/closing motion under an instruction. Namely, by virtue of the prompter 140, a sequence is indicated to the test subject for performing the finger opening/closing motion, prompting the test subject to open the designated finger for N seconds and then close the finger, followed by opening a next finger (N can be set according to actual needs, allowing the test subject to feel a time, or a timer is provided to report a sound). Here, a prompt mode can be the picture and name of each finger (left column in FIG. 4), or a finger number (right column in FIG. 4) of each finger.

Prompt instructions in Case 1 are, for example, one-hand random prompt, such as the index finger of the left hand, the pinky of the right hand, or the like.

Prompt instructions in Case 2 are, for example, one-hand random prompt or two-hand synchronous random prompt. For example, the left index finger quickly opens and closes for 10 seconds, and the two thumbs quickly open and close for 5 seconds, or the like.

Prompt instructions in Case 3 can include at least one of the following a-g.

a. One-hand sequence prompt is performed. Namely, a sequence prompt from left to right or right to left is performed. Here, only one hand is designated for opening/closing motion. For example, pinky, ring finger, . . . thumb.

b. Two-hand synchronism sequence prompt is performed. Namely, a sequence prompt from left to right or right to left is performed. Both hands need to be moved synchronously. For example, the sequence may be pinky, ring finger, . . . thumb.

c. Two-hand sequence prompt is performed. Namely, for both hands, prompt is performed in the order from left to right or right to left. For example: left pinky, left ring finger, . . . right pinky.

d. One-hand random prompt is performed. Namely, single or multiple fingers are randomly prompted, and only one hand is designated for motion. For example: index finger, thumb and pinky, . . . .

e. Two-hand synchronism random prompt is performed. Namely, single or multiple fingers are randomly prompted, and both hands need to be moved synchronously. For example: ring finger, index finger and thumb, . . . .

f. Two-hand complete random prompt is performed. Namely, single or multiple fingers are randomly prompted among 10 fingers, and it is required to open only a designated finger and then close and open a next designated finger. For example: left middle finger and right pinky, right middle finger, index finger and ring finger, . . . .

g. Only descriptive prompt is performed. For example: indication "open the left ring finger till the right index finger in an order from left to right.".

Case 4: A complex motion under instruction is performed. Namely, by virtue of the prompter 140, a test subject will be prompted to perform a complex motion, allowing the test subject to perform an execution according to the prompt.

Prompt instructions in Case 4 can include at least one of the following h-j:

h. One-hand number prompt is performed. Namely, any number within 5 is indicated, and only one-hand gesture shows the corresponding number.

i. Two-hand same number prompt is performed. Namely, any number within 5 is indicated, and both hands gesture performed at the same time shows the corresponding number.

j. Two-hand different number prompt is performed. Namely, for different hands, different numbers are indicated, and both hands gesture performed at the same time shows the corresponding different numbers.

It can be seen that the above exercise items include at least one of one-hand exercise and two-hand exercise, and the one-hand exercise includes at least one of a single-finger exercise and multiple-finger exercises.

In addition, the above exercise items in Case 1 to Case 4 and the corresponding prompt instructions are only examples. Of course, it is also possible to define other exercise items and prompt instructions as needed.

The controller 1210 obtains from the storage 1250 the exercise items generated by the exercise item generator 1221 and their arranging order, as well as prompt instructions, and causes the prompter 140 to indicate the test subject the corresponding prompt instructions according to an arranging order. According to the prompt instruction, the test subject produces a corresponding finger motion. As a result, the controller 1210 obtains the test subject's finger motion data from the finger motion catcher 110 and stores the data in the storage 1250.

The motion parameter calculator 1222, in view of each exercise item generated by the exercise item generator 1221 and in accordance with the finger motion data stored in the storage 1250, calculates the motion parameters characterizing the finger motions.

In the present embodiment, the motion parameters of the respective exercise items are, for example, as follows.

In view of the items in Case 1, the motion parameters may be: a reaction time from the end of the prompt to the beginning of the finger motion, an execution time from the beginning of the finger motion to the completion of the exercise item, a maximum width for each finger to open, a maximum speed for each finger to open, a completion rate, or the like.

In view of the items in Case 2, the motion parameters may be: the number of times for finger opening/closing exercises within a specified time, an interval of time in each finger opening, a maximum height of finger when opening, an average height of respective finger openings, a standard deviation, a total movement distance, a ratio over the highest value of a static state, a maximum speed of finger opening, a maximum acceleration, an average value of a maximum speed/an acceleration each time finger is opened, a standard deviation, an evaluation value on a maximum speed at each finger closing/acceleration, and a variation coefficient. When multiple fingers are moved, motion parameters may also include a deviation time and phase difference once each finger reaches the highest point.

In Case 3 and Case 4, motion parameters may be: a reaction time from the end of prompt to the beginning of finger motion, an execution time from the beginning of finger motion to the completion of an exercise, a maximum width for each finger to open, a maximum speed, an accuracy of finger motion, an interval of time for switching fingers (if an instruction means a single motion). If an instruction means multiple motions, the motion parameters will be the number of opening and closing motions within a specified time, an interval of time at each finger opening, a maximum finger height at finger opening, an average value of respective heights, a standard deviation. Here, motion parameters may also include: a total movement distance, a ratio over the highest value of a static state, a maximum speed when a finger is opened, a maximum acceleration, an average value of maximum speed/acceleration at each finger opening, a standard deviation, an evaluation value of maximum speed/acceleration when finger is closed, a standard deviation, a variation coefficient. When multiple fingers are moving, the motion parameters will be a deviation time and phase difference when each finger reaches the highest point.

The storage 1250 stores in advance a motion parameter database including a variety of data. The finger function evaluator 1223 compares the above-mentioned motion parameter calculated by the motion parameter calculator 1222 with the motion parameter data stored in the storage 1250, and outputs the comparison result through the output terminal 1240.

The finger function evaluator 1223 performs different comparisons according to an input information (exercise purposes in this embodiment).

For example, regarding a situation where rehabilitation training of fingers is required due to trauma, the exercise purpose called "rehabilitation training" is inputted as input information, while the finger function evaluator 1223 uses the historic motion database of the test subject in the motion parameter database to perform a comparison, thereby making it possible to learn the progress of the test subject's finger rehabilitation.

For those who wish to simply evaluate the flexibility of a test subject's fingers, it is required to input an exercise purpose called "flexibility evaluation" as input information. The finger function evaluator 1223 uses the standard motion parameter database in the motion parameter database to perform a comparison. The standard motion parameter database may contain, for example, finger motion parameters of healthy people.

After the above comparison, the controller 1210 outputs a comparison result to a display (not shown) through the output terminal 1240 for displaying, but the present invention should not be limited as such. For example, the comparison result may also be directly displayed on the prompter 140.

Although not shown in the figures, the finger motion exercise assisting apparatus 10 of the present embodiment may further include a finger calibrator that calibrates the finger motion data of a test subject. This is because respective person's finger lengths are different from person to person, so that the finger motion data of different test subjects can be made comparable by calibrating the finger's length data, thereby making it possible to eliminate data deviations caused by the test subject's finger length differences, thus allowing people to more accurately evaluate test subject's finger motion function. A specific calibration method may be, for example, carried out in a manner shown in FIG. 3, so that each finger may be opened (for example, an index finger is opened), and the actual finger length of the test subject and other calculation data can be obtained. If the test subject's hands cannot be freely controlled, an actual index finger length can be obtained with the help of others. In fact, it is also possible for prompt instruction (for performing finger data calibration) to be indicated to the test subject by the prompter 140.

After calibration, the motion parameter calculator 1222 calculates the above motion parameters based on the calibrated finger motion data.

Figure 2:
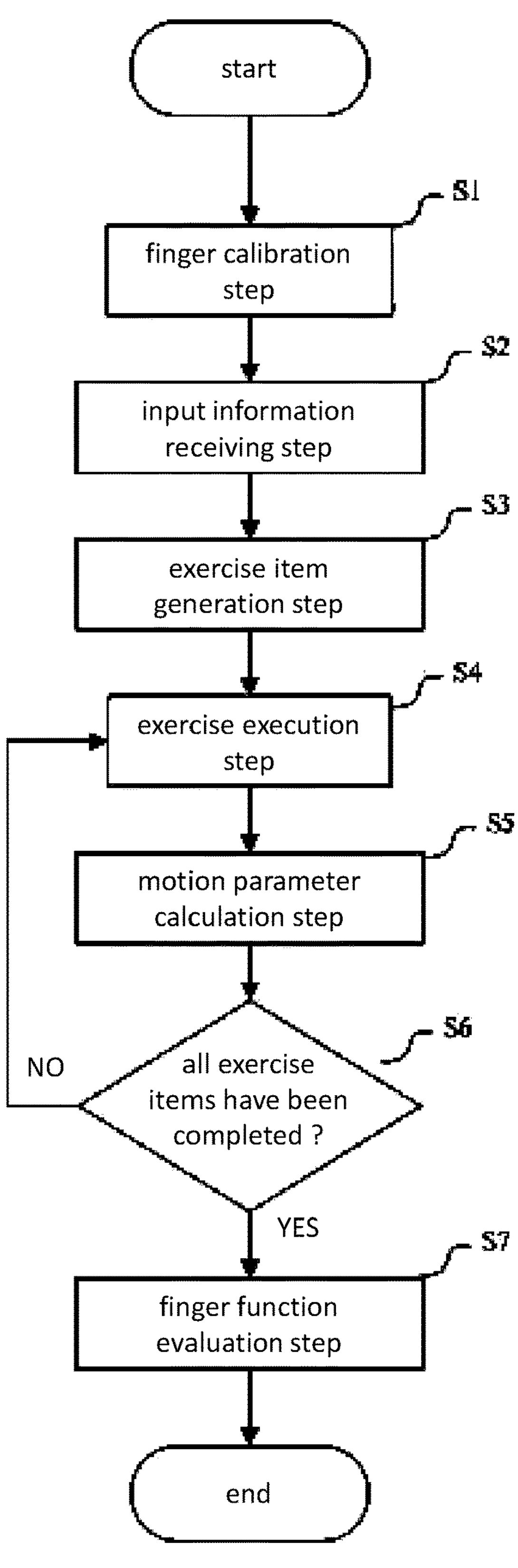
FIG. 2 is a processing flowchart of the finger motion exercise assisting method according to the first embodiment of the present invention.
Figure 3:
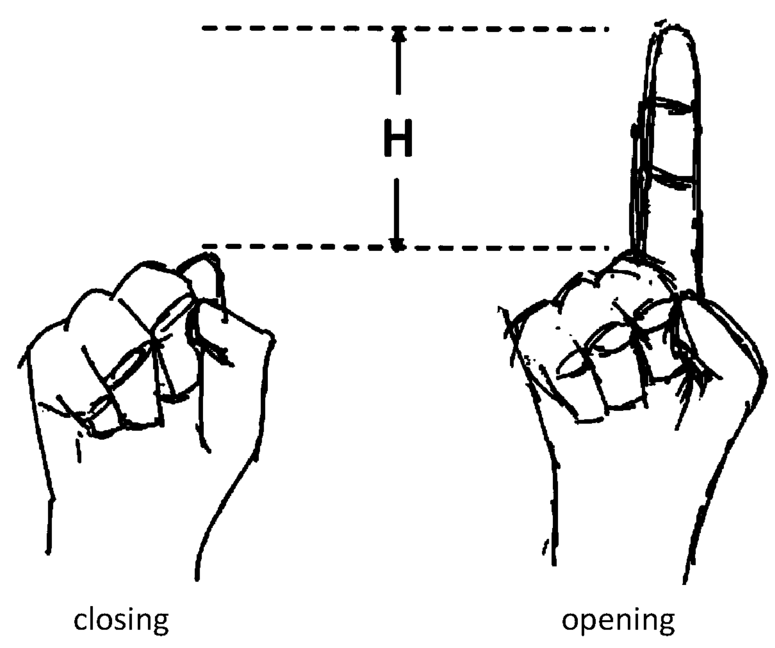
FIG. 3 is a schematic diagram showing the actions of opening and closing the fingers.

FIG. 2 is a processing flowchart of the finger motion exercise assisting method according to the present invention.

First, in step S1 (finger calibration step), the prompter 140 prompts the test subject to perform finger motion data calibration.

Next, in step S2 (input information receiving step), the operator inputs (as input information) an exercise purpose into the operation input receiver 130, which may be a rehabilitation training or a flexibility evaluation.

After selecting an exercise purpose, the process proceeds to step S3 (an exercise item generation step), and generates one or more exercise items and determines an arranging order for these exercise items, in accordance with the exercise purpose selected by the operator. Each exercise item includes one or more prompt instructions for prompting a test subject to perform a finger motion exercise. Then, the exercise items and prompt instructions are stored in the storage 1250.

Next, in accordance with an arranging order of the exercise items generated in step S3, in step S4 (an exercise execution step), the test subject is prompted with a prompt instruction regarding the corresponding exercise items, obtaining finger motion data of the test subject performing finger motion in accordance with prompt instructions, thereby carrying out finger motion exercises.

According to the obtained finger motion data, in step S5 (a motion parameter calculation step), for each generated exercise item it is required to calculate motion parameters characterizing finger motion and to store the parameters in the storage 1250.

Subsequently, the process proceeds to step S6 to determine whether all the exercise items generated in S3 have been completed. If not, the process returns to step S4 to continue a next exercise item until all the exercise items are completed. Then, the process proceeds to step S7.

In step S7 (finger function evaluation step), the above motion parameters are obtained from the storage 1250, and the obtained motion parameters are compared with the database of motion parameters stored in the storage, all in accordance with different exercise purposes.

Figure 5:
FIG. 5 is an evaluation chart corresponding to a "rehabilitation training".
Figure 5:
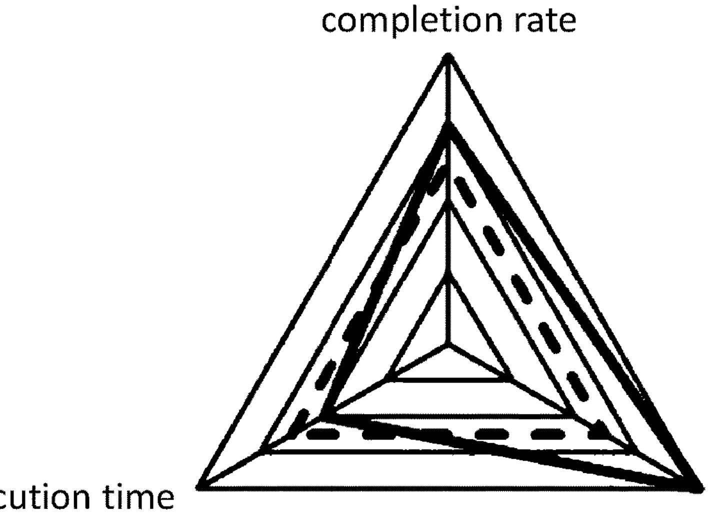

As discussed above, regarding a purpose called "rehabilitation training", for example it is required to compare the current data with the previous data stored in the storage 1250 and to draw an evaluation chart shown in FIG. 5. Alternatively, it is required to read from the storage 1250 the test subject's historical motion parameter data in the motion parameter database, to draw the respective motion parameters into a time series change diagram shown in FIG. 6, and to provide a comprehensive improvement score as a comparison result according to an improvement degree of different motion parameters, followed by outputting the comparison result through the output terminal 1240, thereby figuring out the progress of the test subject's finger rehabilitation.

For an exercise purpose called "flexibility evaluation", it is required to employ the standard motion parameter database in the motion parameter database to perform a comparison, calculate deviations between the motion parameters of the test subject and the data of healthy persons, provide a comprehensive evaluation score as the comparison result, followed by outputting the comparison result to the operator through the output terminal 1240.

In the above-mentioned finger motion exercise assisting method, a finger calibrating step is performed at the beginning, but the present invention should not be limited as such, provided that the finger calibration step can be carried out before the motion parameter calculation step without setting any limitation in a specific position, thereby making it possible to calculate motion parameters in accordance with the calibrated finger motion data in the motion parameter calculation step.

In addition, an execution sequence of the above-mentioned exercise items is not limited to a fixed sequence, but can also include a process of judging and selecting. For example, if a test subject's finger is more severely injured, it is necessary to select the items of Case 1 to perform exercise. When the calculated motion parameters are less than the preset limit values, it may be judged that the selection is not suitable for the follow-up test. At this time, it is necessary to use the output terminal 1240 to output a notification (indicating the information) to the operator, and at the same time to directly terminate the flow procedure. The notification may be displayed on a display (not shown), or directly displayed on the prompter 140.

The above description has enumerated "rehabilitation training" and "flexibility evaluation" as exercise purposes, but present invention should not be limited as such. In fact, it is also possible to perform a finger motion exercise in view of other exercise purposes.

EXAMPLES

The following description will enumerate the compositions of exercise items and their prompt instructions in the embodiments of the present invention.

Example 1

For example, if one wishes to evaluate the finger flexibility of a test subject who uses the finger motion exercise assisting apparatus 10 for the first time, it is necessary to input "first evaluation of flexibility" as an exercise purpose. In this way, the exercise item generator 1221 generates, for example, the following exercise items arranged according to the degree of difficulty: one-hand, simultaneous two-hands, interactive (or random) two-hands.

Case 1→Case 2 (single hand)→a of Case 3→b of Case 3→c of Case 3→Case 2 (simultaneous two-hands)→d of Case 3→e of Case 3→Case 2 (interactive two-hands)→f of Case 3→g of Case 3→h of Case 4→i of Case 4→j of Case 4.

Example 2

If one wishes to conduct a rehabilitation training for fingers injured by fractures, it is required to conduct a basic evaluation of the recovery ability of the fingers. If a related index reaches a certain value after rehabilitation, the injured finger will be caused to have a quick opening/closing motion of Case 2, followed by outputting an improvement effect diagram of each motion parameter.

Example 3

If the interaction between the left and right brains of the test subject is affected by dementia, a basic evaluation on comprehension and finger control ability is performed using Case 1 in accordance with an execution time, completion rate, or the like. After the index reaches a certain value, it is necessary to carry out the follow-up exercise items in the following sequence: Case 2 (simultaneous two-hands)→a-e of Case 3→Case 2 (interactive two-hands)→f-g of Case 3.

Example 4

If healthy elderly people wish to do finger training to prevent dementia, in order to maintain the interest of test subjects, it is possible to perform the following difficult items: Case 2 (simultaneous both-hands), c and e of Case 3, Case 2 (interactive two-hands), f-g of Case 3, h-j of Case 4.

In each of the above-discussed embodiments, it is possible to store the implemented exercise items and exercise results in the storage 1250. When next time you perform finger exercises, you can either start from the beginning or from the position you last stored. In addition, if you are unable to continue the follow-up exercise items due to illness or injury, you can also perform data processing for the completed items.

Second Embodiment

The second embodiment of the present invention will be described below. The overall configuration of the finger motion exercise assisting apparatus 10 according to the second embodiment is substantially the same as that of the first embodiment, and the following description will mainly focuses on their differences.

In the first embodiment, the input information inputted by an operator into the operation input receiver 130 is used as an exercise purpose. Depending on different exercise purposes, it is possible to generate different exercise items and different prompt instructions, and to carry out different data processing. In this embodiment, the input information may be test subject's information, while the test subject's information may include, for example, at least one of the test subject's name, ID, gender, age, height, and weight. If it is necessary to perform a finger motion exercise on a sick or recovered person, the test subjects' information may also include the name of disease.

An action of entering the test subject's information can be regarded as a "login action". According to this embodiment, it is possible to specifically prepare an exercise content (including exercise items and prompt instructions) and to store these data in the storage 1250.

Of course, the input information can also include both the exercise purpose and the test subject's information.

Third Embodiment

The third embodiment of the present invention will be described below. The overall configuration of the finger motion exercise assisting apparatus 10 according to the third embodiment is substantially the same as that of the first embodiment, and the following description will mainly focus on their differences.

In the first embodiment, the input information inputted into the operation input receiver 130 by an operator is an exercise purpose, while in the second embodiment, the input information inputted into the operation input receiver 130 by an operator is a test subject's information. In the present embodiment, the input information is an exercise item generation mode.

The exercise item generation mode includes "automatic generation" and "manual generation". If an operator selects "automatic generation" as a mode of generating exercise item, the exercise item generator 1221 of the finger motion exercise assisting apparatus 10 will automatically generate one or more exercise items and will also determine an arranging order for the exercise items. If an operator selects "manual generation" as a mode of generating exercise item, the exercise item generator 1221 will generate one or more exercise items and will determine an arranging order for the exercise items according to the operator's further selection on the operation input receiver 130. As a result, it is possible to avoid a situation where the stored exercise items do not meet the expectations of the operator and hence it is impossible to perform a finger motion exercise.

Of course, the input information can also include any one or more of the followings: exercise purpose, test subject's information, and an exercise item generation mode.

Figure 7:
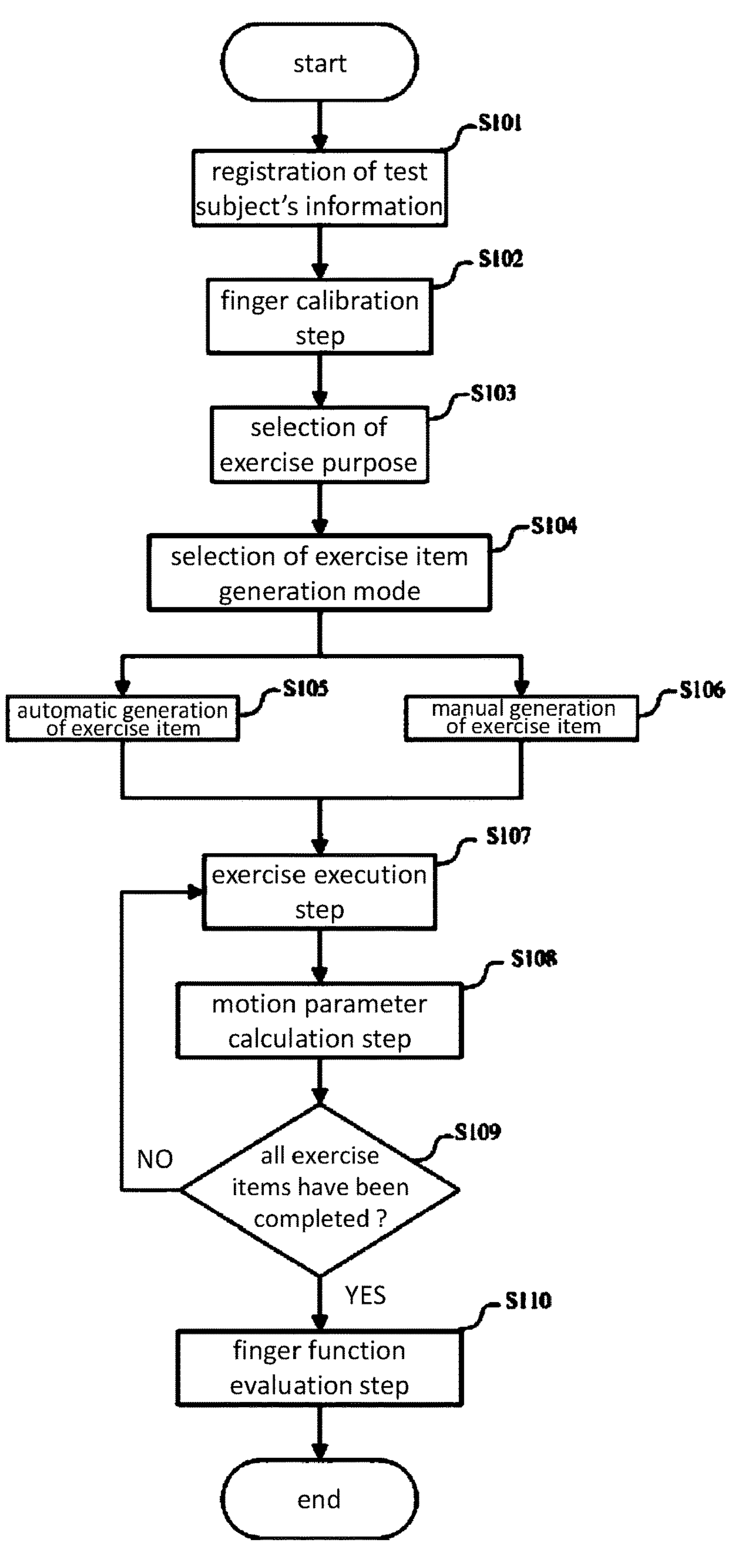
FIG. 7 is a processing flow chart of the finger motion exercise assisting method according to the third embodiment of the present invention.

Next, description will be continued with reference to FIG. 7, which exemplarily shows a processing flowchart of the finger motion exercise assisting method according to the present embodiment.

First, it is required to perform the input information receiving step. In step S101, the test subject's information is registered. In step S103, an exercise purpose is selected, and an exercise item generation mode is selected in step S104. Here, the same finger calibration step as described above can be interspersed between the input information receiving steps, or before or after the input information receiving step. In the finger calibration step S102, the prompter 140 prompts the test subject to perform the finger motion data calibration.

When automatic generation is selected in step S104, the process proceeds to step S105, and the exercise item generator 1221 of the finger motion exercise assisting apparatus 10 automatically generates one or more exercise items and determines an arranging order for the exercise items, in accordance with an exercise purpose, test subject's age, gender, disease name, and the like which are inputted by an operator. For example, when evaluating the finger dexterity of healthy people, finger motion exercise will start from different points according to different ages of test subjects. Namely, those under 60 will start from Case 4, those of 60-70 will start from d of Case 3, those of 70-80 will start from c of Case 3, those over 80 will start their finger exercises from a of Case 3.

When manual generation is selected in step S104, the process proceeds to step S106, and the exercise item generator 1221 will generate one or more exercise items according to the operator's selection on the operation input receiver 130 and will determine an arranging order for these exercise items.

Next, as in the first embodiment, in accordance with an arranging order of the exercise items generated in step S105 or S106, the test subject is prompted with prompt instruction for the corresponding exercise items in the exercise execution step S107, followed by catching the finger motion data of the test subject's finger motion performed according to the prompt instruction, thereby performing finger motion exercises.

According to the obtained finger motion data, in step S108 (motion parameter calculation step), regarding each generated exercise item, the motion parameter characterizing the motion of the finger is calculated and stored in the storage 1250.

Subsequently, the process proceeds to step S109 to determine whether all the exercise items generated in step S105 or S106 have been completed. If not, the process returns to step S107 to continue the next exercise item until all the exercise items are completed. Then, the process proceeds to step S110.

In step S110 (finger function evaluation step), the above motion parameters are obtained from the storage 1250, and based on the test subject's information registered in step S101 and the exercise purpose selected in step S103, the obtained motion parameters are respectively compared with the motion parameter data stored in the storage 1250.

For example, if the ID of the entered test subject's information is "AA", the age is 65, the gender is "Male", and the disease name is "Alzheimer's disease", in view of an exercise purpose called "rehabilitation training", the obtained motion parameters of the test subject are compared with the last obtained motion parameter of the test subject whose ID is "AA" (stored in the storage 1250), followed by drawing an evaluation chart such as that shown in FIG. 5 and outputting the same to the prompter 140. On the other hand, in view of an exercise purpose called "flexibility evaluation", the obtained motion parameters of the test subjects are compared with the motion parameter data of healthy persons (in an age of 60-70 and having a gender of "male") stored in the storage 1250, followed by calculating deviation values between various motion parameters of the test subject and the healthy person's data, providing a comprehensive evaluation score as the comparison result and outputting the same to the prompter 140.

Figure 6:
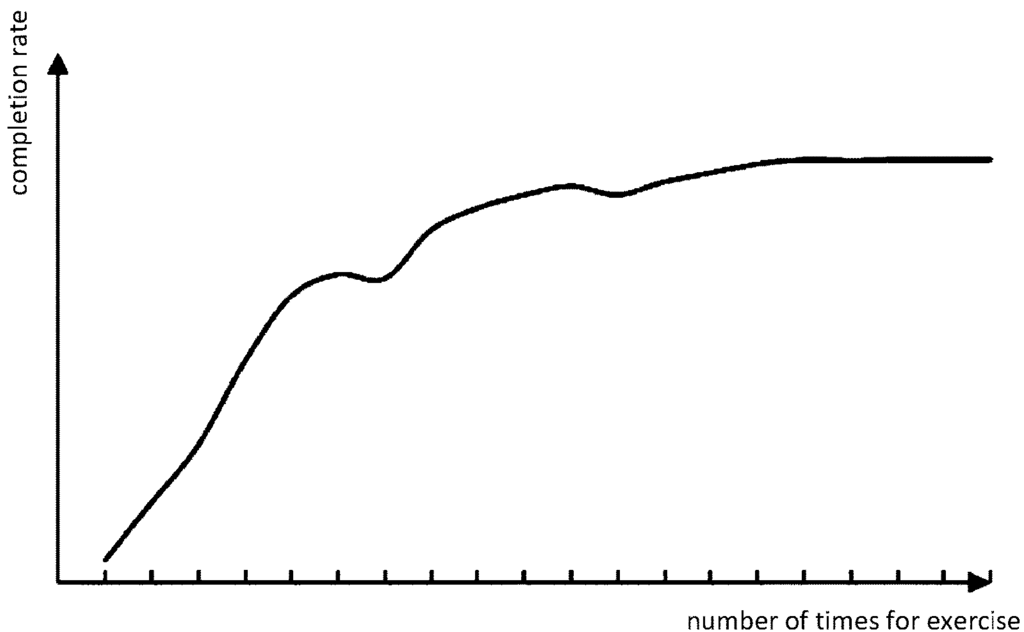
FIG. 6 is a time series change graph corresponding to a "rehabilitation training".

In another example, if the ID in the test subject's input information is "BB", the age is 23, the gender is "female", and the disease name is "index finger fracture", it is possible to take "rehabilitation training" as an exercise purpose, to compare the obtained motion parameters of the test subject with the previous motion parameters of the test subject whose ID is "BB" (stored in the storage 1250), and to draw a time-series change diagram such as that shown in FIG. 6, followed by outputting the same to the display (not shown). With respect to an exercise purpose called "flexibility evaluation", the obtained motion parameters of the test subject are compared with the motion parameter database of healthy people within an age of 20-30 and having a gender of "female" (stored in the storage 1250), followed by calculating deviation values between individual's motion parameters and the healthy person's data, thus providing a comprehensive evaluation score as a comparison result and outputting the same to a display (not shown).

In addition, as described in the first embodiment, although the "finger calibration step" is located at the position of step S102, the present invention should not be limited as such. As long as the finger calibration step is performed before the motion parameter calculation step, it is possible to calculate motion parameters in the motion parameter calculation step in accordance with the calibrated finger motion data.

The embodiments and examples of the present invention have been described above, but these embodiments and examples are merely illustrative and are not intended to limit the scope of the invention. These embodiments can be implemented in other various forms, and various omissions, substitutions, changes, and combinations can be made within the scope not departing from the gist of the invention. While these embodiments and their modifications are included in the scope and spirit of the invention, they are also included in the inventions prescribed in the claims appended below and their equivalent scopes.

The invention claimed is:

1. A finger motion exercise assisting apparatus, which is used to assist a test subject in finger motion exercise, said apparatus comprising:

a set of magnetic sensors configured to be disposed on a finger of a test subject configured to acquire first finger motion data of the finger of the test subject during opening/closing exercises as the finger performs a motion according to a prompt instruction and second finger motion data of the finger of the test subject as the finger is moved from a closed position in which the finger is fully contracted to an open position in which the finger is fully extended, a finger motion analyzer including a processor, coupled to the magnetic sensor set, and a memory coupled to the processor, the memory storing instructions that when executed by the processor, configure the processor to:

receive input information of an operator, said input information including: an exercise purpose, a selection of an automatic generation or a manual generation as an exercise item generation mode, and at least one of the test subject's age, gender, and disease name, receive the first finger motion data and the second finger motion data from the set of the magnetic sensors, calibrate finger motion data of the finger of the test subject based on a finger length of the test subject, which is obtained based on the second finger motion data, generate two or more exercise items, each exercise item including one or more of the prompt instructions, according to the selection of the automatic generation or the manual generation as the exercise item generation mode included in the input information and when the exercise item generation mode is automatic generation, automatically generate the two or more exercise items and determine an arranging order for the exercise items in accordance with the operator's input information including the exercise purpose, and the at least one of the test subject's age, gender, and disease name, and when the exercise generation mode is manual generation, generate the two or more exercise items and determine an arranging order for the exercise items, in accordance with the operator's selection, in accordance with the first finger motion data and with respect to each generated exercise item, calculate a motion parameter characterizing a finger motion, in accordance with the input information, compare the motion parameter with a motion parameter database stored in the memory, and output a comparison result, wherein the finger length and calibration information based on the finger motion data calibrated based on the finger length of the test subject are used to evaluate a performance of the test subject for comparison purposes.

2. The finger motion exercise assisting apparatus according to claim 1, wherein the exercise purpose is rehabilitation training or flexibility evaluation, wherein the processor is configured to:

when the exercise purpose is rehabilitation training, use the test subject's historical motion parameter data in the motion parameter database to perform the comparison, and when the exercise purpose is flexibility evaluation, use a standard motion parameter database in the motion parameter database to perform the comparison.

3. The finger motion exercise assisting apparatus according to claim 1, wherein the exercise item includes at least one of a single-hand exercise and a two-hand exercise, said single-hand exercise including at least one of a single-finger exercise and a multiple-finger exercise.

4. The finger motion exercise assisting apparatus according to claim 3, wherein the prompt instruction is at least one of: one-hand sequence prompt, one-hand random prompt, one-hand number prompt, two-hand synchronism sequence prompt, two-hand sequence prompt, two-hand synchronism random prompt, two-hand complete random prompt, two-hand same number prompt, two-hand different number prompt, and descriptive prompt.

5. A finger motion exercise assisting method, which is used to assists a test subject in finger motion exercise, said method comprising:

acquire, by a set of magnetic sensors configured to be disposed on a finger of a test subject, first finger motion data of the finger of the test subject during opening/ closing exercises as the finger performs a motion according to a prompt instruction and second finger motion data of the finger of the test subject as the finger is moved from a closed position in which the finger is fully contracted to an open position in which the finger is fully extended;

receiving input information, said input information including: an exercise purpose, a selection of an automatic generation or a manual generation as an exercise item generation mode, and at least one of the test subject's age, gender, and disease name;

generating two or more exercise items, each exercise item including one or more of the prompt instructions, according to the selection of the automatic generation or the manual generation as the exercise item generation mode included in the input information and when the exercise item generation mode is automatic generation, the two or more exercise items and the arranging order for the exercise items are automatically generated and determined in accordance with the operator's input information including the exercise purpose, and the at least one of the test subject's age, gender, and disease name, and when the exercise item generation mode is manual generation, the two or more exercise items and the arranging order for the exercise items are generated and determined, respectively, in accordance with the operator's selection, in accordance with the exercise items and the determined arranging order, indicating to the test subject the prompt instruction, and acquiring finger motion data of the test subject who performed a finger motion in accordance with the prompt instruction;

in accordance with the finger motion data and with respect to each generated exercise item, calculating a motion parameter characterizing a finger motion;

in accordance with the input information, comparing the motion parameter with a motion parameter database, and outputting a comparison result; and calibrating the finger motion data of the test subject based on the test subject's finger length, which is obtained based on the second finger motion data;

wherein the finger length and calibration information based on the finger motion data calibrated based on the finger length of the test subject are used to evaluate a performance of the test subject for comparison purposes.

6. The finger motion exercise assisting method according to claim 5, wherein the exercise purpose is rehabilitation training or flexibility evaluation, wherein when the exercise purpose is rehabilitation training, a historical motion parameter data of the test subject in the motion parameter database is used for the comparison, and wherein when the exercise purpose is flexibility evaluation, the standard motion parameter database in the motion parameter database is used for the comparison.

7. The finger motion exercises assisting method according to claim 5, wherein the exercise item includes at least one of a single-hand exercise and a two-hand exercise, with the single-hand exercise including at least one of a single-finger exercise and a multiple-finger exercise.

8. The finger motion exercises assisting method according to claim 7, wherein the prompt instructions include at least one of: one-hand sequence prompt, one-hand random prompt, one-hand number prompt, two-hand synchronism sequence prompt, two-hand sequence prompt, two-hand synchronism random prompt, two-hand complete random prompt, two-hand same number prompt, two-hand different number prompt, and descriptive prompt.

* * * * *